United States Patent

Falk

[11] Patent Number: 5,524,497
[45] Date of Patent: Jun. 11, 1996

[54] ADDITIVE FOR MOLTEN METAL SAMPLER

[75] Inventor: Richard A. Falk, Hillsboro Beach, Fla.

[73] Assignee: Midwest Instrument Co., Inc., Hartland, Wis.

[21] Appl. No.: 391,203

[22] Filed: Feb. 21, 1995

Related U.S. Application Data

[63] Continuation of Ser. No. 67,715, May 26, 1993, Pat. No. 5,447,080.

[51] Int. Cl.⁶ .................................................. G01N 1/12
[52] U.S. Cl. .................................................. 73/864.58
[58] Field of Search ........................ 73/864.56, 864.57, 73/864.58, 864.82

[56] References Cited

U.S. PATENT DOCUMENTS

| | | | |
|---|---|---|---|
| 2,819,956 | 1/1958 | Strauss | 420/415 |
| 3,063,286 | 11/1962 | Nerheim . | |
| 3,295,171 | 1/1967 | Strange et al. | 73/864.58 X |
| 3,452,602 | 7/1969 | Hackett | 164/4 X |
| 3,546,921 | 12/1970 | Bourke et al. | 75/130 X |
| 3,646,816 | 3/1972 | Hance et al. | 73/DIG. 9 X |
| 3,686,949 | 8/1972 | Hackett | 73/DIG. 9 X |
| 3,783,694 | 1/1974 | Otte et al. . | |
| 3,805,621 | 4/1974 | Falk | 73/DIG. 9 X |
| 3,818,762 | 6/1974 | Kraus et al. | 117/231 X |
| 3,844,172 | 10/1974 | Jeric | 73/DIG. 9 X |
| 3,946,594 | 3/1976 | Surinx | 73/DIG. 9 X |
| 4,002,072 | 1/1977 | Collins | 73/864.58 |
| 4,010,649 | 3/1977 | Falk | 73/DIG. 9 X |
| 4,037,478 | 7/1977 | Cure | 73/DIG. 9 X |
| 4,059,996 | 11/1977 | Curé | 73/DIG. 9 X |
| 4,069,717 | 1/1978 | Falk | 73/864.56 |
| 4,107,393 | 8/1978 | Frantzreb, Sr. et al. | 428/558 |
| 4,121,749 | 10/1978 | Cure | 228/173 A |
| 4,140,019 | 2/1979 | Falk | 73/DIG. 9 X |
| 4,222,269 | 9/1980 | Falk . | |
| 4,261,740 | 4/1981 | Plessers | 73/864.58 X |
| 4,274,284 | 6/1981 | Hance . | |
| 4,570,496 | 2/1986 | Falk | 73/864.58 |
| 4,698,095 | 10/1987 | Ototani et al. | 75/304 |
| 5,014,561 | 5/1991 | Falk et al. | 73/864.53 |
| 5,057,149 | 10/1991 | Conti et al. | 75/377 |
| 5,187,991 | 2/1993 | Baerts | 73/864.56 |
| 5,305,658 | 4/1994 | Magee, Jr. | 73/864.82 |
| 5,393,497 | 2/1995 | Haber et al. | 73/864.82 X |
| 5,447,080 | 9/1995 | Falk | 73/864.58 |

*Primary Examiner*—Thomas P. Noland
*Attorney, Agent, or Firm*—Ryan, Maki, Mann & Hohenfeldt

[57] ABSTRACT

A sampling cavity for sampling molten metals includes a cavity body for receiving a measured sample of a molten metal, and, an insert containing a material for promoting carbide formation in the molten metal as it cools, the insert being in the form of an enclosed capsule formed of thin polymeric walls containing the material in finely divided solid form. The insert may be adhered within a fill inlet passage or attached at the bottom of a cup sampler having an open top either by being adhered directly to the cavity surface or by being supported in a supporting means such as a pair of fingers projecting from the bottom of the cavity.

10 Claims, 2 Drawing Sheets

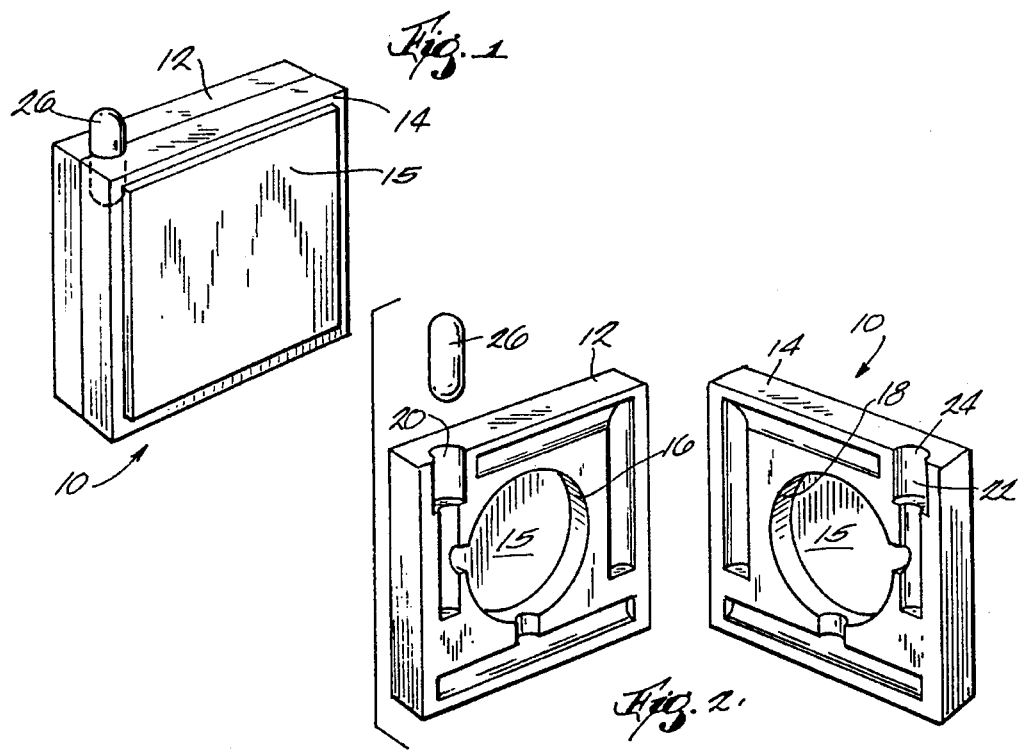
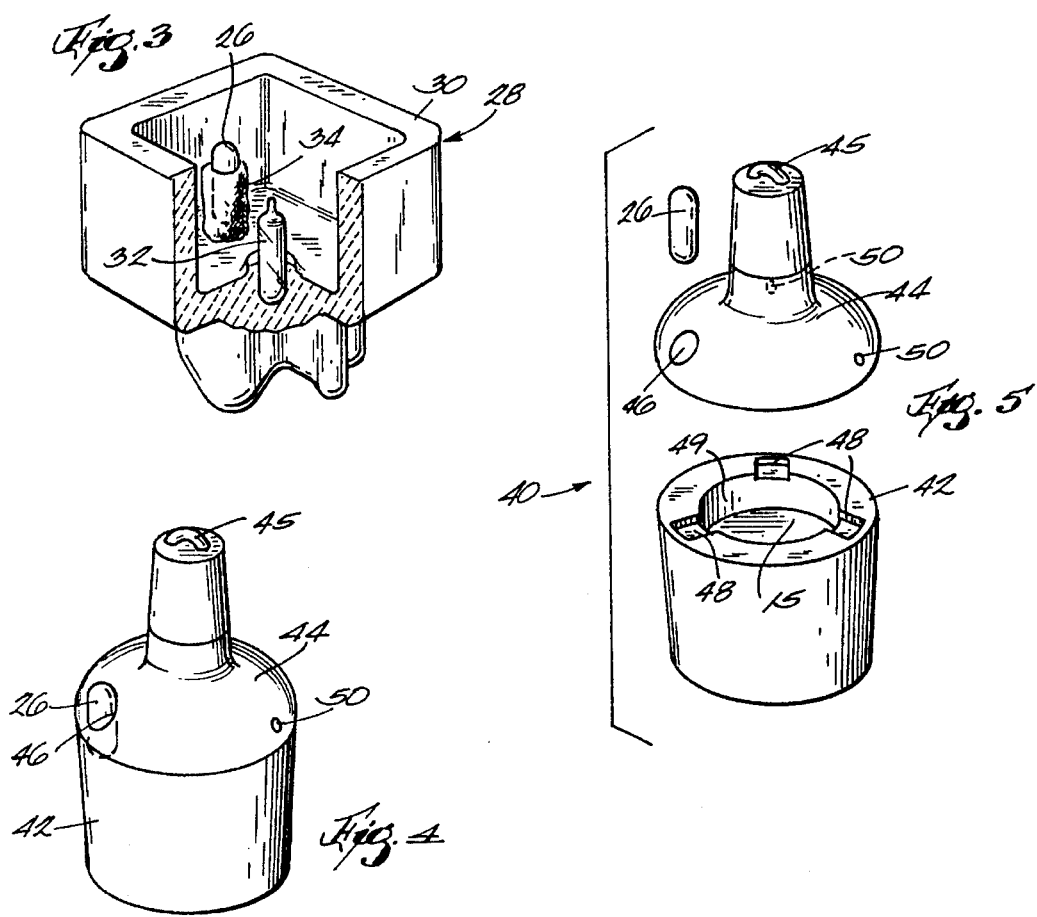

ADDITIVE FOR MOLTEN METAL SAMPLER

This is a continuation of application Ser. No. 08/067,715 filed on May 26, 1993, and now U.S. Pat. No. 5,447,080.

BACKGROUND OF THE INVENTION

The present invention relates to molten metal samplers. More specifically, the invention relates to devices having cavities for obtaining samples of a molten metal for the purpose of determining the composition or characteristics of the molten metal and wherein provision is made for adding a material for promoting carbide formation in the molten metal as it cools.

To spectrographically analyze a molten metal to determine its composition, it is common practice to obtain small sample castings or samples for analysis. In order to make an accurate analysis of molten iron, it is desirable to obtain samples of uniform composition, density and structure such as white iron, in which the carbon remains dissolved or interspersed in the metal in the form of a carbide instead of precipitating out in the form of graphite, which results in gray iron or spheroidal/nodular iron. Materials which deter graphite formation, such as tellurium, bismuth or antimony have been heretofore coated on mold surfaces fixed in the filling area, or have been placed in the mold in the form of an insert, for example, as described in Falk U.S. Pat. No. 4,570,496 issued Feb. 18, 1986. U.S. Pat. No. 4,059,996 shows a technique using a "blob" of such material in a cup type mold cavity. A device for providing an additive such as tellurium to a mold for obtaining samples for spectrographic analysis is described in U.S. Pat. No. 5,057,149 wherein the additive is placed between two flat metal layers. A need has, however, continued to exist for improved techniques for consistently obtaining uniform, homogeneous dense, fine grained metallurgical white iron samples, even if the metal contains high carbon contents or has a high carbon equivalent. Carbon equivalent is defined in U.S. Pat. No. 3,546,921, issued Dec. 15, 1970.

SUMMARY OF THE INVENTION

An important aspect of the present invention is to provide an economical, low cost device for adding tellurium or a similar material to a cavity for obtaining samples of a molten metal for analysis in which carbide formation within the metal is promoted. A further aspect is to provide for such a device wherein an insert is used which provides for the addition of an accurately measured quantity of tellurium to a sampling cavity in a sample mold or cup, thereby assuring consistently accurate analyses, ie., an accurately measured amount of tellurium is added to a measured volume of molten iron. Another advantage provided by the invention is the use of a low-temperature melting capsule to provide immediate rapid dispersion and uniform mixing of the additive into the metal sample. A further advantage is to provide such an device which uses a low mass of capsule material thus avoiding agitation of the metal. The invention further avoids use of coating materials or binders which tend to delay dissolution and to contaminate the molten metal sample.

A still further aspect of the invention relates to improvement of safety to workers by completely sealing the tellurium additive or similar hazardous material, and avoiding chipping, breaking or abrading off of such materials. Further advantages are provided by the ease of color coding of capsules to indicate different effective amounts of additives. A controlled amount of carbide formation promoting material is thus utilized for each use of a sampling cavity. A further aspect of the invention involves the ability to easily wedge or adhere the capsule in a cup or fill tube, the light weight of the capsule providing position stability. The filling opening of a spectrographic sampling mold then acts as a mixing chamber or area in which the carbide formation promoting material is mixed with the metal being sampled as it enters the mold cavity.

A still further advantage is the ability to use an accurately dimensioned capsule containing an additive for the secondary purpose of providing a combustible capping system for a fill tube in which the capsule is adhered thus eliminating the need for a separate cap on the fill opening. Optionally the insert can be located within the sample cavity of the mold, instead.

Briefly summarized, the present invention provides a device for sampling molten metals that includes a sample cavity for receiving a measured sample of a molten metal, and, an insert containing a material for promoting carbide formation in the molten metal as it cools, the insert being in the form of an enclosed capsule formed of thin-walled organic material, said insert containing the carbide formation promoting material in finely divided solid form. The insert may be formed of any heat consumable material such as an organic polymer, paper, cellulose or the like. The material should be of a low, consistent mass and have a low melting point or low flash point relative to the temperature of molten iron. The insert may be positioned within a fill inlet passage in the case of an immersion fill type sampling mold or adhered by means of a ceramic cement or other adhesive to an interior surface of a cup type sampler having an open top. In accordance, with a further embodiment a supporting means such as a pair of supporting fingers can be provided in a sampling cavity to support the insert in a fixed position, for example, spaced above the bottom of the cavity.

The cavity for immersion sampling molten metals includes a mold body having first and second mold halves. Each of the mold halves has peripheral edges and the halves define a sample cavity having a fill inlet passage when the mold halves are assembled together. The mold halves further define an opening for flow therein of molten metal during immersion of the mold into molten metal, which opening is connected to the sample cavity inlet so that molten metal can flow from the opening into the sample cavity. In the preferred embodiment, the mold may be supported in a cardboard tube to assist in the immersion of the mold into molten metal. Details of such devices as further described in my U.S. Pat. Nos. 4,069,717 and 4,140,019, which are incorporated by reference.

In the case of cup type samplers, the cooling curve of the molten metal sample is monitored by means of a thermocouple or similar temperature measuring device that extends into the sample cavity, in order to determine the composition of the metal, based on the form of the cooling curve. In accordance with still further aspects of the invention a plurality of capsules can be used to provide a predetermined amount of additive material in the sample cavity. In the case of such cup type samplers one or more pairs of fingers integral with the bottom of the sample cavity can be used to support the insert a short distance above the bottom of the cavity. The molten metal will thus be able to entirely engulf the insert to facilitate rapid and thorough introduction and of the additive into the metal sample to thereby inoculate the metal with the additive.

In accordance with the preferred embodiment, the carbide formation promoting material is tellurium. Other such materials, can however, be substituted.

BRIEF DESCRIPTION OF DRAWINGS

The invention will further be described in the following detailed description and accompanying drawings wherein:

FIG. 1 is a perspective view of a mold and mold insert of this invention;

FIG. 2 is a perspective view of the mold of FIG. 1 disassembled;

FIG. 3 is a perspective view of a different cavity using the invention;

FIG. 4 is a perspective view of yet another form of cavity using the invention;

FIG. 5 is a perspective view of the mold of FIG. 4 disassembled;

DETAILED DESCRIPTION OF THE PREFERRED EMBODIMENTS

Figure 6:
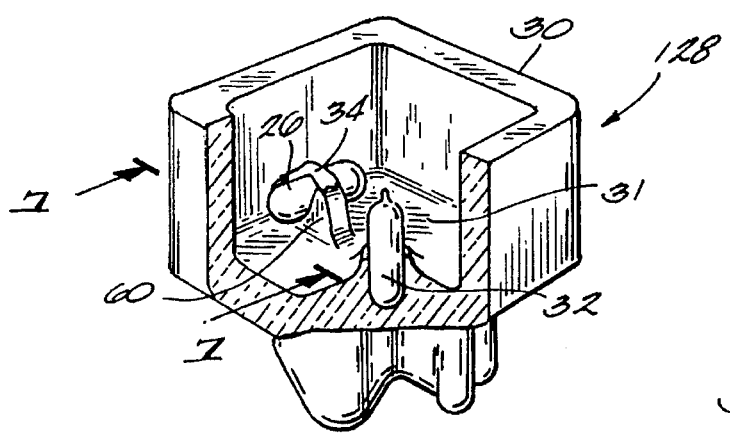
FIG. 6 is a perspective view of a further embodiment of the invention with parts broken away and in cross section; and, FIG. 7 is a cross sectional view taken along Line 7—7 of FIG. 6.

A mold assembly 10 is seen in FIGS. 1 and 2 in assembled and separated condition, respectively. Mold 10 includes mold halves 12 and 14 preferably formed from a ceramic material and mold-closing chill plates 15 of heat conductive metal such as steel in order to provide for rapid conduction of heat from the molten metal sample. A sample cavity is provided by aligned openings 16 and 18 in mold halves 12 and 14. Any conventional clamping or attaching system can be used for closing and holding the halves 12 and 14 of the mold together. Inlet passage 20, 22 is provided for introduction of molten metal into cavity 16. A widened opening 24, as shown, is provided for flow into the mold of molten metal to be sampled during immersion of the mold into molten metal and serves as a housing for an insert 26. Insert 26 contains a material for promoting carbide formation in the molten metal as it cools. Preferably the insert is in the form of an enclosed capsule formed of thin walls formed of an organic material, such as a polymeric resin, containing the material, such as tellurium, in finely divided solid form.

The insert may be adhered within fill inlet passage 24 by means of an adhesive..Insert 26 is also clamped in place when the mold halves 12 and 14 are assembled, and the use of an adhesive is thus not required in all cases. Flow of molten metal through tube into opening 24 during immersion of the mold into molten metal causes instantaneous melting of the walls of insert 26 and release of the contents into the molten metal sample as it flow into the mold cavity 16, 18. The metal that flows down through opening 20 into cavity 16 becomes mixed with a sufficient amount of the tellurium in order to inhibit graphite formation during solidification and thus promote the formation of the desired white iron structure. After cooling of the metal, the mold halves 12, 14 are separated to yield a sample disc of metal for spectrographic analytical testing.

FIG. 3 shows another form of sampling device in the form of an open top container or sample cup 28, defined by side walls 30 and bottom 31. A measuring device 32 is positioned in bottom 31 for measurement of characteristics such as temperature, dissolved oxygen, carbon or silicon content of the metal sample. An adhesive material 34 retains an insert 26 in the sample cavity of cup 28. While sample cup 28 is illustrated as being of a square configuration, such cups are also formed of other shapes, such as round.

Another form of sampling mold 40 in connection with which the invention can be used is shown in FIGS. 4 and 5. Mold 40 (like mold 10) is particularly adapted for immersion in a molten metal bath to withdraw a sample. Mold 40 is formed by a cup-shaped bottom portion 42 that is closed by a capped portion 44. A cardboard tube is attached to cap portion 44 for handling the mold when it is immersed in a molten metal bath. An opening 46 for receiving molten metal is formed in cap portion 44 and also serves as a housing for an insert 26 which contains finely divided carbide forming material such as tellurium. Internal notches 48 provide flow paths for molten metal to reach a sample cavity 49 in the base portion 42 of mold 40. Smaller openings 50 are provided in capped portion 44 to permit the escape of air from the interior of the mold as it fills with molten metal. Chill plates 15 are preferably located in the bottom of cavity 49 and in cap 44.

Immersion of mold 40 in a molten metal bath to a depth at which opening 46 is totally submerged causes rapid or virtually instantaneous combustion of the outer skin of capsule 26 and allows the finely divided solid carbide forming material within the capsule to flow with the molten metal into chamber 49, and to become uniformly mixed with the molten metal to promote carbide formation therein.

It will be noted that in the case of molds 10 and 40 that capsule 26 serves both to form a capsule for containing the finely divided additive to the metal sample and also to perform the secondary function of acting as a closure or capping system for the sampling mold opening.

The capsule 26 is preferably formed of two telescoping halves in the nature of a pharmaceutical capsule. However, an entirely sealed capsule can also be used. The walls of the capsule can be formed of any thin, low mass combustible, non-contaminating material that disintegrates by melting and/or combustion to release the contents of the capsule. Examples of suitable materials include gelatin, thermoplastic polymers, paper or similar substances. The particularly preferred materials in addition to gelatin are polymers such as a polyolefin, polyvinylchloride or polyvinylalcohol. The substitution of various other polymeric materials will be readily apparent to those skilled in the art. It is preferred that the walls of capsule 26 be formed of thermoplastic material so that the material instantaneously or rapidly melts upon contact with the molten metal. However, if desired, particularly in the case of an open top sampling mold such as shown in FIG. 3, the capsule could, if desired, be formed of a thermosetting polymeric material or paper, which would burn away instead of melt when contacted by the molten metal. Insert 26 can also take the form of a small sealed plastic bag or wrap, or, alternatively, a tiny cardboard tube. It will be apparent to those skilled in the art that other materials having a low mass that rapidly melts (such as aluminum or steel foil) or combusts can be used so long as it does not contaminate the sample melt.

Figure 7:
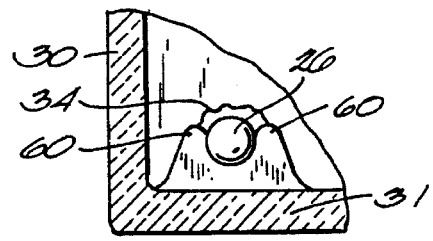

In the further embodiments seen in FIGS. 6 and 7, a sample cup of mold 128 is generally similar to mold 28. Similarly numbered parts are the same as those referred to with respect to FIG. 3. However, a pair of fingers 60 is formed integrally with the bottom 31 of sample cup 128. It will be noted that when insert 26 is adhered between fingers 60, that the insert can be supported off the surface of bottom 31. Insert 26 may be, for example, spaced a distance of about one-eighth inch off of bottom 31. It has been found that when insert 26 is thus raised, that when molten metal is poured into cup 128 the insert 26 is completely engulfed by the molten metal and rapid or instantaneous dispersion of the additive powder contained therein occurs. If desired, more than one pair of fingers 60 can be provided for use of more than one insert 26. Also, the fingers may be formed in different configurations than those shown. In accordance with a still further embodiment, insert 26 can be wedged between a single finger 60 and side wall 30, if desired.

It will be apparent to those skilled in the art that numerous modifications of the aforedescribed preferred embodiment can be made. For example, mold chill plate inserts 15 can be formed from various metals, for example, ductile iron, copper, or steel. With the addition of the carbide formation promoting material it is possible to utilize somewhat less heat conductive material for mold inserts 15 than would otherwise be necessary. Previous methods of adding carbide formation promoting materials to mold often required contaminating binders or coating compositions which retard the release of the carbide former. In contrast, the present invention permits use of the materials in pure powder form which disperse more rapidly into the metal. It will also be appreciated by those skilled in the art that in addition to tellurium, various other carbide formation promoting materials can be substituted, for example, coating containing bismuth, antimony, boron, cesium or other similar materials known in the art or mixtures thereof.

In addition to the foregoing, various other modifications falling within the scope and spirit of the invention will be apparent to those skilled in the art.

I claim:

1. A sampling device for sampling molten metals comprising:

a sampling cavity for receiving a measured sample of a molten metal having side and bottom walls, and, an insert containing a material for promoting carbide formation in the molten metal as it cools, said insert being in the form of a thin-walled enclosed capsule formed of combustible organic material containing said material in finely divided solid form, the walls of said capsule being formed of a material that disintegrates when contacted by a molten metal at least one surface portion of said insert being attached to said cavity at a location spaced away from said bottom wall.

2. A device according to claim 1 wherein said cavity is defined by mold halves of an immersion sampler, said mold halves having peripheral edges and openings in said mold halves to define a sample cavity having a fill inlet passage when said mold halves are assembled together, said capsule being positioned within said fill inlet passage to substantially close said passage, said capsule being melted or combusted when molten metal flows therethrough to thereby open said passage and to release said material into said metal.

3. A device according to claim 1 wherein said carbide formation promoting material is selected from the group consisting of tellurium, bismuth, cesium, antimony, boron or mixtures thereof.

4. A device according to claim 1 wherein said cavity is in the form of an open thermal analysis cup and said capsule is affixed to an interior surface thereof.

5. A device according to claim 1 wherein the body of said cavity is configured in the form of a cup having a closure, said closure having at least one fill inlet passage, and wherein said insert is positioned within said fill inlet passage forming a temporary closure therefor.

6. A device according to claim 1 wherein a plurality of said capsules containing said material are attached to the interior said cavity.

7. A device according to claim 1 wherein said capsule is formed of a material that melts when contacted by molten metal.

8. A device according to claim 7 wherein the walls of said capsule comprise a thermoplastic organic polymer.

9. A device according to claim 7 wherein the walls of said capsule comprise gelatin.

10. A device according to claim 1 wherein said capsule is formed of a material that combusts when contacted by molten metal.

\* \* \* \* \*

UNITED STATES PATENT AND TRADEMARK OFFICE
CERTIFICATE OF CORRECTION

PATENT NO. : 5,524,497
DATED : June 11, 1996
INVENTOR(S) : Falk

It is certified that error appears in the above-indentified patent and that said Letters Patent is hereby corrected as shown below:

Column 6, Line 24   Before "forming" insert -- thereby --

Column 6, Line 27   After "interior" insert -- of --

Signed and Sealed this

Tenth Day of September, 1996

Attest:

BRUCE LEHMAN

Attesting Officer      Commissioner of Patents and Trademarks